US00PP15279P2

(12) United States Plant Patent
Hansen

(10) Patent No.: US PP15,279 P2
(45) Date of Patent: Oct. 26, 2004

(54) *ASTER* PLANT NAMED 'VICTORIA GABY'

(50) Latin Name: *Aster novi-belgii*
Varietal Denomination: Victoria Gaby

(75) Inventor: Erwin Hansen, Hornslet (DE)

(73) Assignee: Asterklubben, Årslev (DK)

( * ) Notice: Subject to any disclaimer, the term of this patent is extended or adjusted under 35 U.S.C. 154(b) by 0 days.

(21) Appl. No.: 10/770,215

(22) Filed: Feb. 2, 2004

(51) Int. Cl.[7] ..... A01H 5/00
(52) U.S. Cl. ..... Plt./355
(58) Field of Search ..... Plt./355

*Primary Examiner*—Kent Bell
(74) *Attorney, Agent, or Firm*—C. A. Whealy

(57) ABSTRACT

A new and distinct cultivar of potted *Aster* plant named 'Victoria Gaby', characterized by its upright and outwardly spreading plant habit; dark green foliage; freely flowering habit; and decorative-type inflorescences with purple-colored ray florets.

1 Drawing Sheet

Botanical classification/cultivar designation: *Aster novi-belgii* cultivar Victoria Gaby.

BACKGROUND OF THE INVENTION

The present Invention relates to a new and distinct cultivar of potted *Aster* plant, botanically known as *Aster novi-belgii* and hereinafter referred to by the name 'Victoria Gaby'.

The new *Aster* is a product of a planned breeding program conducted by the Inventor in Årslev, Denmark. The objective of the breeding program is to create new potted *Aster* cultivars with uniform plant growth habit, desirable floret colors, and good postproduction longevity.

The new *Aster* originated from a cross-pollination made by the Inventor in Årslev, Denmark in July, 2000, of a proprietary *Aster* selection identified as code number 24.15, not patented, as female, or seed, parent with the *Aster* cultivar Loke Viking, disclosed in U.S. Plant Pat. No. 10,359, as the male, or pollen, parent. The new *Aster* was discovered and selected by the Inventor as a single flowering plant within the progeny of the stated cross-pollination grown in a controlled environment in Årslev, Denmark. The selection of this plant was based on its uniform plant growth habit and desirable inflorescence form and ray floret color.

Asexual reproduction of the new *Aster* by vegetative tip cuttings was first conducted in Årslev, Denmark during June, 2001. Asexual reproduction by cuttings has shown that the unique features of this new *Aster* are stable and reproduced true to type in successive generations.

SUMMARY OF THE INVENTION

The cultivar Victoria Gaby has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Victoria Gaby'. These characteristics in combination distinguish 'Victoria Gaby' as a new and distinct *Aster*.

1. Upright and outwardly spreading plant habit.
2. Dark green foliage.

3. Freely flowering habit.
4. Decorative-type inflorescences with purple-colored ray florets.

Plants of the new *Aster* are more uniform than plants of the female parent selection. In addition, plants of the new *Aster* differ from plants of the female parent selection in ray floret coloration.

Plants of the new *Aster* have more darker green-colored leaves than plants of the male parent, the cultivar Loke Viking. In addition, plants of the new *Aster* differ from plants of the cultivar Loke Viking in ray floret coloration as plants of the cultivar Loke Viking have red purple-colored ray florets.

Plants of the new *Aster* can be compared to plants of the cultivar Victoria Fanny, disclosed in U.S. Plant Pat. No. 13,360. In side-by-side comparisons conducted in Broby, Denmark, plants of the new *Aster* differed from plants of the cultivar Victoria Fanny in the following characteristics:

1. Plants of the new *Aster* had smaller leaves than plants of the cultivar Victoria Fanny.
2. Plants of the new *Aster* and the cultivar Victoria Fanny differed in ray florets coloration as plants of the cultivar Victoria Fanny had lavender blue-colored ray florets.

BRIEF DESCRIPTION OF THE PHOTOGRAPHS

The accompanying colored photographs illustrate the overall appearance of the new *Aster* showing the colors as true as it is reasonably possible to obtain in colored reproduction of this type. Colors in the photographs may differ from the color values cited in the detailed botanical description which accurately describe the colors of the new *Aster*.

The photograph at the top of the sheet comprises a side perspective view of a typical flowering plant of 'Victoria Gaby'.

The photograph at the bottom of the sheet comprises a close-up view of the upper (left) and lower (right) surfaces of typical inflorescences and leaves of 'Victoria Gaby'.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the summer in Broby, Denmark, in a glass-covered greenhouse and under conditions which approximate those generally used in commercial potted *Aster* production. During the production of these plants, day and night temperatures were about 20 to 21° C. One cutting was planted in 10-cm containers and pinched once. Plants were about 12 weeks old when the photographs and the botanical description were taken.

Botanical classification: *Aster novi-belgii* cultivar Victoria Gaby.

Parentage:

*Female, or seed, parent.*—Proprietary *Aster novi-belgii* selection identified as code number 24.15, not patented.

*Male, or pollen, parent.*—*Aster novi-belgii* cultivar Loke Viking, disclosed in U.S. Plant Pat. No. 10,359.

Propagation:

*Type.*—Terminal vegetative cuttings.

*Time to initiate roots.*—Summer: About 12 days at 21° C. Winter: About 13 days at 21° C.

*Root description.*—White, close to 155D; fine; fibrous.

*Rooting habit.*—Freely branching.

Plant description:

*Appearance.*—Herbaceous decorative-type potted *Aster*. Stems upright and outwardly spreading; rounded plant habit. Appropriate for 10 to 15-cm containers.

*Plant height.*—About 14 to 18 cm.

*Plant width.*—About 18 to 22 cm.

*Lateral branches (peduncles).*—Length: About 6 to 12 cm. Diameter: About 3 mm. Strength: Strong. Angle: Erect to about 45° from vertical. Texture: Slightly pubescent. Color: 137A.

*Foliage description.*—Arrangement: Alternate; sessile. Length: About 3.5 to 4.5 cm. Width: About 8 to 12 mm. Shape: Lanceolate. Apex: Acute. Base: Cuneate. Margin: Ciliate. Texture, upper and lower surfaces: Glabrous, smooth; leathery. Color: Developing and fully expanded foliage, upper surface: 147A; venation, close to 147A. Developing and fully expanded foliage, lower surface: 137B; venation, close to 137B.

Inflorescence description:

*Appearance.*—Decorative-type inflorescence form with narrowly obovate-shaped ray florets. Inflorescences terminal or axillary. Disc and ray florets develop acropetally on a capitulum. Inflorescences not fragrant. Inflorescence persistent.

*Flowering response.*—Under natural season conditions, plants flower in the summer in Broby, Denmark.

*Postproduction longevity.*—Inflorescences maintain good color and substance for about three weeks in an interior environment.

*Quantity of inflorescences.*—About six to nine inflorescences develop per lateral branch.

*Inflorescence bud.*—Height: About 4 to 6 mm. Diameter: About 4 to 7 mm. Shape: Ovoid. Color: Close to 137A.

*Inflorescence size.*—Diameter: About 3 to 3.5 cm. Depth (height): About 1.3 to 1.8 cm. Diameter of disc: About 8 to 10 mm.

*Ray florets.*—Number of ray florets per inflorescence/arrangement: About 125 to 175 arranged in about five to six whorls. Length: About 1.5 to 2.2 cm. Width: About 1 to 3 mm. Shape: Narrowly obovate. Apex: Rounded. Base: Attenuate. Margin: Entire. Texture, upper and lower surfaces: Smooth, glabrous. Orientation: Initially upright, then mostly horizontal. Aspect: Straight to slightly concave. Color: When opening and fully opened, upper surface: 77A; color becoming closer to 77A to 77B with development. When opening and fully opened, lower surface: 83D.

*Disc florets.*—Arrangement: Massed at center of receptacle. Number of disc florets per inflorescence: About 10 to 20. Length: About 1.1 mm. Width: Less than 1 mm. Shape: Tubular, elongated. Apex: Acute. Color: Close to 145C.

*Phyllaries.*—Quantity per inflorescence: About 20 to 30. Length: About 2 mm. Width: Less than 1 mm. Shape: Narrowly obovate. Apex: Acuminate. Base: Truncate. Texture, upper and lower surfaces: Smooth, glabrous. Color upper and lower surfaces: 137A.

*Reproductive organs.*—Androecium: Present on disc florets only. Quantity per disc floret: One. Anther shape: Narrowly obovate. Anther length: About 1 mm. Anther color: 8C. Pollen amount: Moderate. Pollen color: 12A. Gynoecium: Present on both ray and disc florets. Quantity per floret: One. Stigma shape: Bifurcate. Stigma color: 3D.

*Seed/fruit.*—Seed and fruit production have not been observed.

Disease/pest resistance: Resistance to pathogens and pests common to *Asters* has not been observed on plants grown under commercial greenhouse conditions.

It is claimed:

1. A new and distinct cultivar of potted *Aster* plant named 'Victoria Gaby', as illustrated and described.

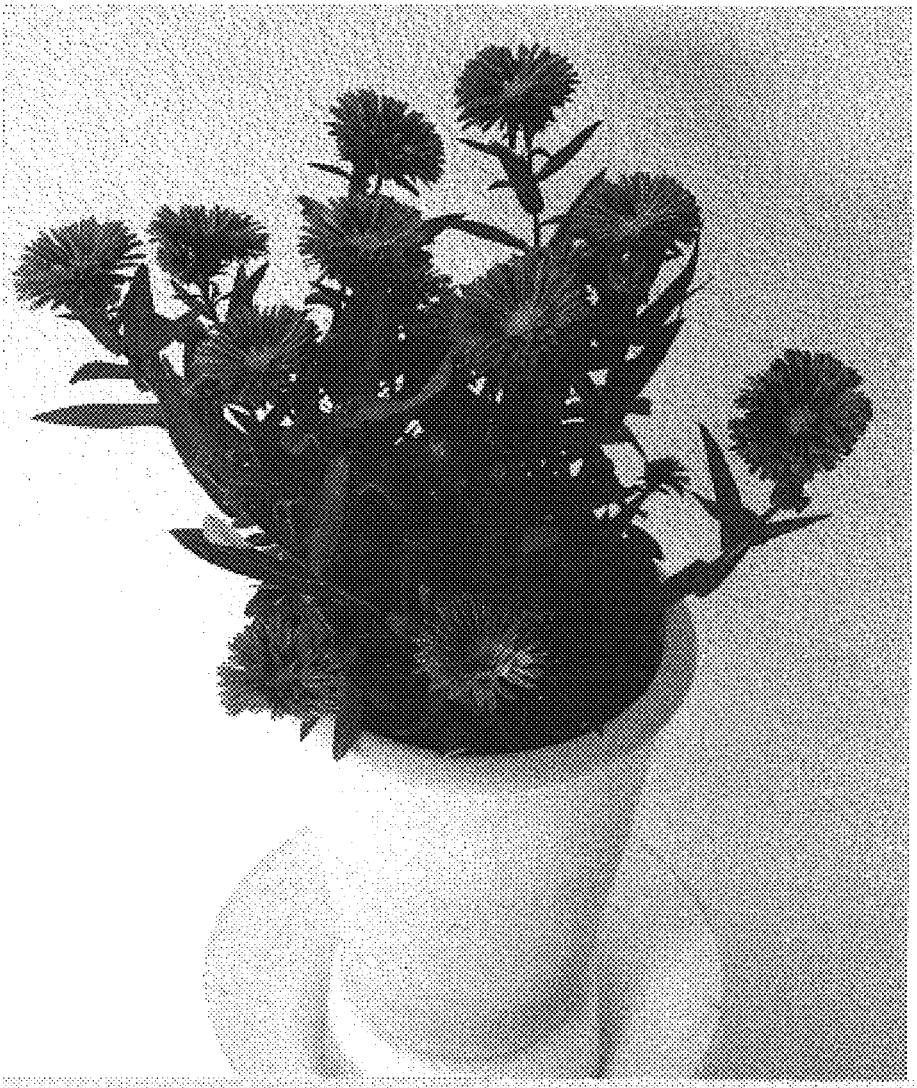
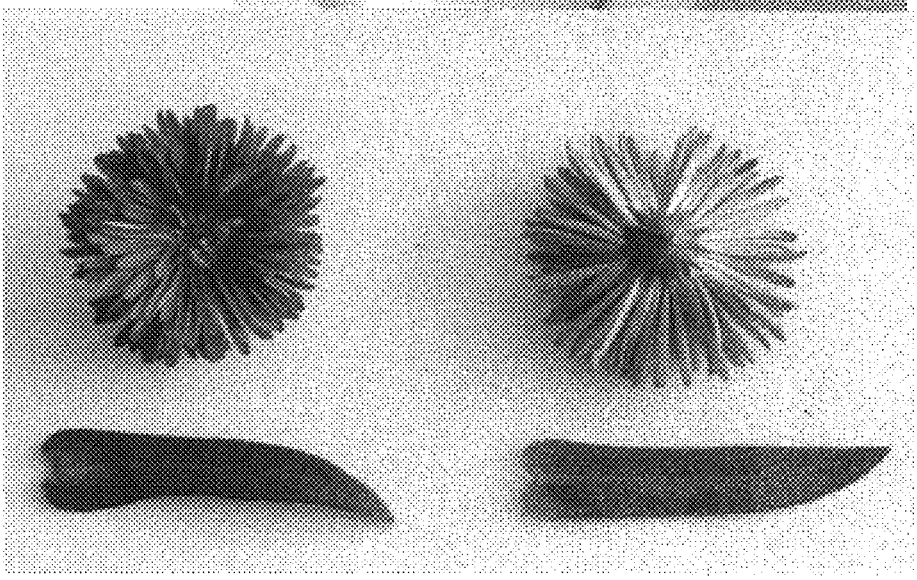

* * * * *